United States Patent [19]
Fox et al.

[11] Patent Number: 6,111,105
[45] Date of Patent: Aug. 29, 2000

[54] PROCESSES AND INTERMEDIATES FOR PREPARING 3-(1-PIPERAZINYL)-1,2-BENZISOTHIAZOLE

[75] Inventors: Darrell E. Fox, Pawcatuck; John F. Lambert, North Stonington; Terry G. Sinay, Preston; Stanley W. Walinsky, Mystic, all of Conn.

[73] Assignee: Pfizer, Inc., New York, N.Y.

[21] Appl. No.: 09/068,285

[22] PCT Filed: Oct. 11, 1996

[86] PCT No.: PCT/IB96/01079

§ 371 Date: Oct. 15, 1998

§ 102(e) Date: Oct. 15, 1998

[87] PCT Pub. No.: WO97/17336

PCT Pub. Date: May 15, 1997

Related U.S. Application Data

[60] Provisional application No. 60/006,301, Nov. 7, 1995.
[51] Int. Cl.[7] .................. C07D 417/04; C07D 295/26; C07D 275/04
[52] U.S. Cl. ............................. 544/368; 548/209
[58] Field of Search .............. 544/368; 548/209

[56] References Cited

U.S. PATENT DOCUMENTS

| | | | |
|---|---|---|---|
| 5,679,827 | 10/1997 | Goda et al. | 558/425 |
| 5,756,806 | 5/1998 | Goda et al. | 558/425 |
| 5,861,511 | 1/1999 | Goda et al. | 544/368 |

FOREIGN PATENT DOCUMENTS 2 163 432  2/1986  United Kingdom.

OTHER PUBLICATIONS

Yevich et al, *J. Med. Chem.* vol. 29, p. 359–369, 1986.

Saji et al, *Chemical Abstracts*, vol. 122, No. 31512K (Abstract for JP 06 220030 Aug. 9, 1994) 1995.

*Primary Examiner*—Emily Bernhardt
*Attorney, Agent, or Firm*—Peter C. Richardson; Gregg C. Benson; B. Timothy Creagan

[57] ABSTRACT

The present invention relates to processes for the preparation of 3-(1-piperazinyl)-1,2-benzoisothiazole or its pharmaceutically acceptable salt and to novel intermediates used in the process.

18 Claims, No Drawings

PROCESSES AND INTERMEDIATES FOR PREPARING 3-(1-PIPERAZINYL)-1,2-BENZISOTHIAZOLE

This application claims the benefit of U.S. Provisional Application No. 60/006,301, filed Nov. 7, 1995.

BACKGROUND OF THE INVENTION

The present invention relates to processes for the preparation of 3-(1-piperazinyl)-1,2-benzisothiazole or one of its pharmaceutically acceptable salts and to novel intermediates used in said processes. 3-(1-Piperazinyl)-1,2-benzisothiazole is a key intermediate useful for the preparation of 5-(2-(4-(1,2-benzisothiazol-3-yl)-1-piperazinyl) ethyl)-6-chloro-1,3-dihydro-2H-indol-2-one (ziprasidone). This compound has neuroleptic activity.

U.S. Pat. No. 4,831,031, issued May 16, 1989, which is hereby incorporated by reference in its entirety, discloses 5-(2-(4-(1,2-benzisothiazol-3-yl)-piperazinyl)ethyl)-6-chloro-1,3-dihydro-2H-indol-2-one hydrochloride, which has the formula

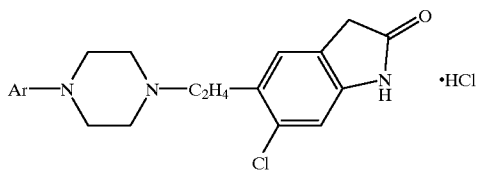

wherein Ar is benzisothiazol-3-yl, in the hemihydrate form (hereafter "the hemihydrate").

U.S. Pat. No. 5,312,925 issued May 17, 1994, which is hereby incorporated by reference in its entirety, refers to the monohydrates hydrochloride salt of ziprasidone, processes for its preparation, and pharmaceutical compositions and methods of treating psychotic disorders.

U.S. Pat. No. 5,359,068, issued Oct. 25, 1994, which is hereby incorporated by reference in its entirety, refers to processes and intermediates for the preparation of ziprasidone.

U.S. Pat. No. 5,206,366, issued Apr. 27, 1993, which is hereby incorporated by reference in its entirety, refers to an aqueous based process for preparing ziprasidone.

U.S. Pat. No. 4,590,196, issued May 20, 1986, refers to 1-(1,2-benzisothiazol-3-yl)piperazine, which is the penultimate intermediate made by the processes of the present invention.

Japanese Patent Publication 6,220,030 published Aug. 9, 1994 refers to the preparation of 3-amino-1,2-benzisothiazole derivatives from the reaction of bis(2-cyanophenyl)disulphide derivatives with metal amides followed by treatment with an oxidizing agent.

SUMMARY OF THE INVENTION

The present invention relates to a compound of the formula

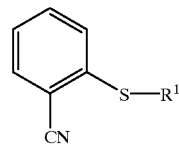

IIa wherein $R^1$ is

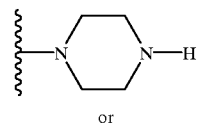

a or

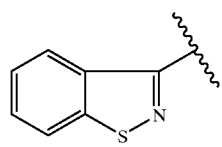

b

The present invention also relates to a process for preparing a compound of the formula

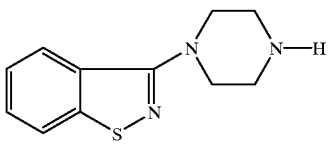

I comprising reacting a compound of the formula

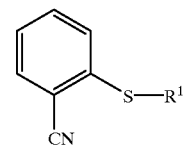

II wherein $R^1$ is

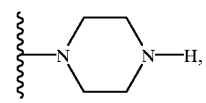

a or

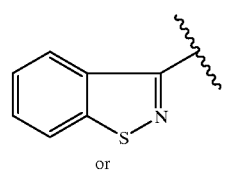

b

-continued

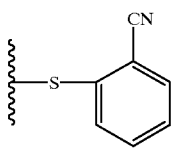

c with piperazine at a temperature from about 80° C. to about 170° C. Preferably, $R^1$ is a group of the formula "c". Preferably, the amount of piperazine is about 2 mole equivalents to about 15 mole equivalents relative to the amount of the compound of formula II. Most preferably, the amount of piperazine is about 10 mole equivalents relative to the amount of a compound of formula II.

A preferred embodiment o the present invention relates to a process for converting a compound of formula II into a compound of formula I in the presence of a piperazine clearing agent. Suitable piperazine clearing agents are isopropanol, pyridine or t-butanol, preferably isopropanol. Preferably about 1.2 volumes (a relative proportion (mL/gm) to the weight of the compound of formula II) of the piperazine clearing agent is used.

A preferred embodiment of the present invention also relates to a process for converting a compound of formula II wherein $R^1$ is

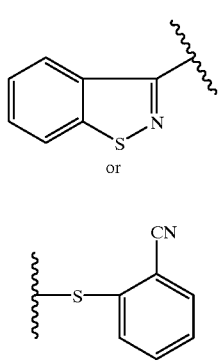

into a compound of formula I, further comprising reacting said compound of the formula II with piperazine in the presence of a thiol oxidizing agent. Suitable thiol oxidizing agents are dimethyl sulfoxide, air, copper(II) salts, bisulfite, metabisulfite or hydrogen peroxide, preferably dimethyl sulfoxide. Preferably, the amount of said thiol oxidizing agent, dimethyl sulfoxide, is 2–4 mole equivalents relative to the compound of formula II.

The most preferred embodiment of the present invention relates to a process for converting a compound of formula II, wherein $R^1$ is the group "c", into a compound of the formula I, comprising reacting said compound of the formula II with piperazine, a piperazine clearing agent (most preferably isopropanol), and a thiol oxidizing agent (most preferably dimethyl sulfoxide).

"Piperazine clearing agent," when used herein, refers to a solvent that when refluxing is capable of dissolving piperazine that has solidified in the head space and vapor spaces of the reaction vessel. One of ordinary skill in the art will appreciate that piperazine solidifies at about 108° C. and as such will solidify in any area of the reaction vessel that is at or below that temperature. One of ordinary skill in the art will also understand that the areas of the reaction vessel most likely to promote piperazine solidification are those areas above the solution level of the reaction.

The area above the solution in the reaction vessel but confined within the reactor walls is included within the reaction domain and is called the head space of the reaction vessel. Vapor space refers to the space in and around the various feeder lines to and from the reaction vessel.

Copper(II) salts when used herein refers to copper chloride ($CuCl_2$), copper bromide ($CuBr_2$) or copper sulfate ($CuSO_4$).

Bisulfite when used herein refers to sodium bisulfite ($NaHSO_3$) or potassium bisulfite ($KHSO_3$).

Metabisulfite when used herein refers to sodium metabisulfite ($Na_2S_2O_5$) or potassium metabisulfite ($Na_2S_2O_5$).

DETAILED DESCRIPTION

The compounds of the formula I and ziprasidone can be prepared as described in the following reaction schemes and discussion. Unless otherwise indicated, compounds of the formulae I, II and IIa, and the group $R^1$ in the reaction schemes and discussion are as defined above.

SCHEME 1

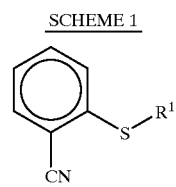

II

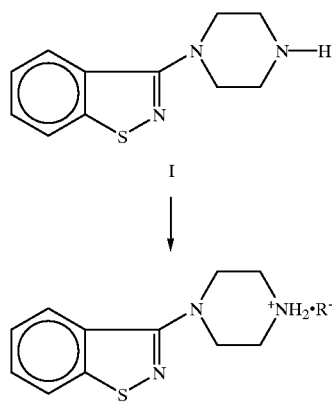

I

Ia

SCHEME 2

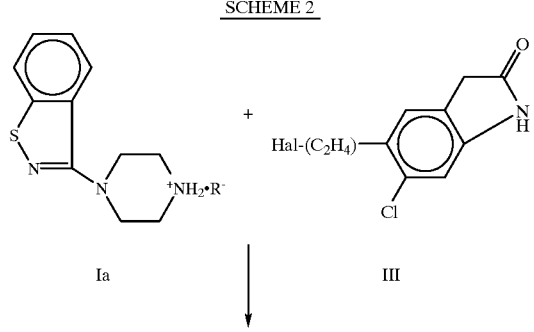

Ia III

-continued

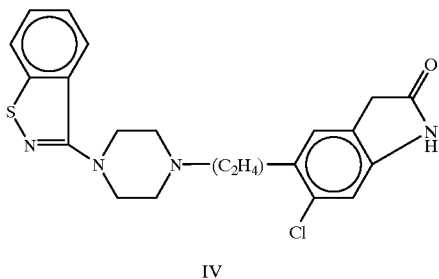

IV

Scheme 1 refers to the preparation of intermediates of the formula I or Ia which can be converted into the final product, ziprasidone, by the methods of Scheme 2.

Referring to Scheme 1, a compound of the formula II, wherein $R^1$ is c

is commercially available or can be prepared according to the method of Japanese Patent Publication 6,220,030, published Aug. 9, 1994.

A compound of the formula II wherein $R^1$ is a

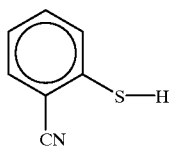

may be prepared by reacting a compound of the formula

V

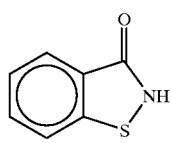

with about 1 to about 10 equivalents of piperazine, preferably about 2 to about 5 equivalents of piperazine is used. The temperature of the aforesaid reaction is between about 25° C. to about 105° C., preferably about 65° C. The reaction time varies from about 1 hour to about 20 hours, preferably from about 2 to about 6 hours.

The compound of formula V is prepared from an amide of the formula

VI

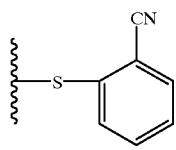

by reaction with about 1 to about 3 equivalents of a chlorinating agent such as phosphorous oxychloride (POCl$_3$), phosphorous trichloride (PCl$_3$), or phosphorous pentachloride (PCl$_3$) in reaction inert solvent. Preferably about 1,2 equivalents of phosphorous oxychloride is used as the chlorinating agent. Suitable solvents include dimethylformamide, dimethylacetamide, or pyridine, preferably dimethylformamide. The reaction time of the aforesaid reaction is from about 1 to about 6 hours, preferably about 3.5 hours. The reaction is performed at a temperature from about 30° C. to about 100° C. preferably about 70° C.

The compound of the formula VI is commercially available.

Compounds of the formula II, wherein $R^1$ is b

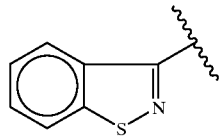

can be prepared by reacting bis(2-cyanophenyl)disulfide with a compound of the formula

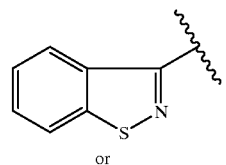

in a reaction inert solvent. Suitable reaction inert solvents include isopropanol, ethanol, or tetrahydrofuran, preferably isopropanol. The temperature of the aforesaid reaction is about 50° C. to about 120° C. The reaction time of the aforesaid reaction is about 1 hour to about 3 hours, preferably about 2 hours.

A compound of the formula II, wherein $R^1$ is a

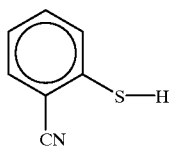

b

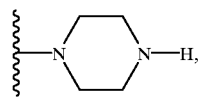

or c

can be converted into a compound of the formula I by reaction with from about 2 to about 20 equivalents of piperazine (preferably anhydrous). The preferred amount of piperazine is the amount of piperazine that minimizes bis substitution of the free amine of the piperazine group of the compound of the formula I. The preferred $R^1$ is

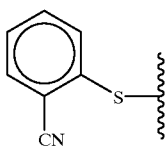

When $R^1$ is a group of the formula "c", as depicted above, the preferred amount of piperazine is about 6 to 10 equivalents, most preferably about 10 equivalents. The temperature of the aforesaid reaction is between about 76° C. and 200° C., preferably about 120° C. The reaction time varies depending on the temperature at which the reaction is run. As the reaction temperature is increased the reaction time is decreased. When the reaction is run at about 80° C., only small amounts of product are formed after 2 days. When the reaction is run at about 200° C. the vessel must be pressurized to prevent loss of the piperazine and the clearing agent and the ensuing reaction time is about 1 hour. When the reaction is performed at high temperatures, the internal reaction vessel pressure is between about 50 to 60 psi and as such is well within the standard pressure capacities for commercial reactors. When the reaction is performed at the ideal temperature of about 120° C. the reaction time is about 24 hours.

The reaction between a compound of the formula II, wherein $R^1$ is

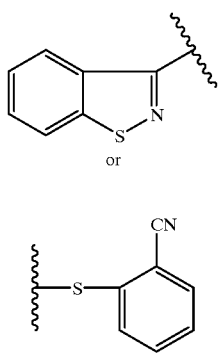

and piperazine generates a thiol by-product of the formula

VII

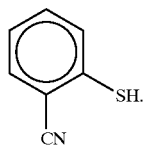

A preferred embodiment of the reaction involves the in situ oxidation of the compound of formula VII into a compound of the formula II, wherein $R^1$ is

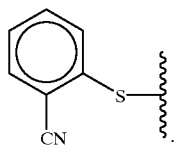

This in situ oxidation is facilitated by adding from about 1 to about 10 equivalents, preferably 4 equivalents, of an oxidant to the reaction vessel. Suitable oxidants include dimethyl sulfoxide, air, copper (II) salts, bisulfite, metabisulfite or hydrogen peroxide, preferably dimethyl sulfoxide. When dimethyl sulfoxide is the oxidant, preferably about 2 to 5 equivalents are used in the reaction.

In another preferred embodiment of the reaction about 0.5 to about 5 volume of a piperazine clearing agent is added to the reaction vessel so as to prevent piperazine from solidifying in the head space and vapor lines of the reaction vessel. Suitable piperazine clearing agents have boiling points in the range of the about 70° C. to about 130° C. such as isopropanol or t-butanol, pyridine, toluene or diglyme, preferably isopropanol. Preferably about 1,2 volumes (a relative proportion (mL/gm) to the weight of the compound of formula II) of the piperazine clearing agent is used.

A compound of the formula I can be converted to the more stable pharmaceutically acceptable salts of the formula Ia, wherein R is a pharmaceutically acceptable anion conjugate of a pharmaceutically acceptable acid, by treatment of the free base of formula I with a pharmaceutically acceptable acid of the formula RH in a polar solvent. Suitable acids of the formula RH are those which form non-toxic acid addition salts, e.g., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, meleate, fumarate, gluconate, saccharate, benzoate, methanesulfonate and pamoate [i.e., 1,1'-methylene-bis-(2-hydroxy-3-naphthoate)] salts. Preferably the acid is hydrochloric acid. Suitable solvents include lower alcohols, such as methanol, ethanol, isopropanol or t-butanol, toluene, ethers such as diethyl ether or tetrahydrofuran, or mixtures of the above solvents. Preferably the solvent is a mixture of isopropanol and toluene.

The conversion of the compound of formulae I or Ia to ziprasidone follows the processes described in U.S. Pat. No. 4,831,031, 5,206,366 or 5,359,068, which issued on May 16, 1989, Apr. 27, 1993 and Oct. 25, 1994 respectively.

Scheme 2 refers to the preparation of ziprasidone from compounds of the formula I or Ia according to the processes described in U.S. Pat. No. 4,831,031, issued May 16, 1989. Specifically, a compound of the formula I or Ia is reacted with a compound of the formula III wherein Hal is fluoro, chloro, bromo or iodo. This coupling reaction in generally conducted in a polar solvent such as a lower alcohol, for instance ethanol, dimethylformamide or methyl isobutyl ketone, and in the presence of a weak base such as a tertiary amine base, for instance triethylamine or diisopropylethylamine. Preferably, the reaction is performed in the further presence of a catalytic amount of sodium iodide, and a neutralizing agent for hydrochloride such as sodium carbonate. The reaction is preferably conducted at the reflux temperature of the solvent used.

Alternatively, Scheme 2 also refers to the conversion of compounds of formula I or Ia into ziprasidone by the methods of U.S. Pat. No. 5,206,366, issued Apr. 27, 1993.

Specifically, a compound of formula I or Ia is reacted with a compound of formula III, wherein Hal is fluoro, chloro, bromo or iodo. This coupling reaction is conducted in refluxing water with a hydrohalic acid neutralizer.

Alternatively, compounds of the formula I can be converted to ziprasidone by the methods described in U.S. Pat. No. 5,359,068, issued Oct. 25, 1994.

Specifically, compounds of the formula I may be reacted with a compound of the formula

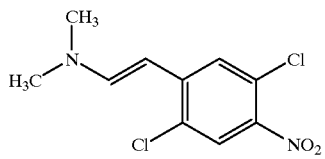

VIII in the presence of a $(C_1-C_6)$ alkanoic acid to form the compound of the formula

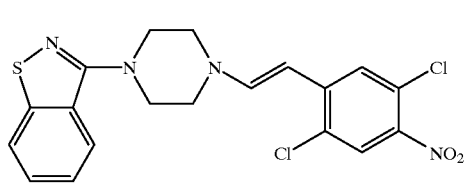

IX

The compound of the formula IX can then be treated with a reducing agent to form the compound of the formula

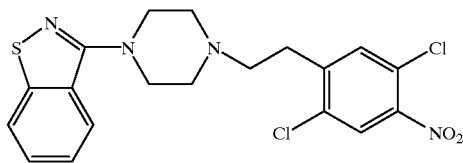

X

The compound of the formula X can then be treated with a compound of the formula $R^3-CH_2-CO_2R^3$ wherein $R^2$ is $CO_2R^3$ or CN and $R^3$ is $(C_1-C_6)$alkyl to form a compound of formula

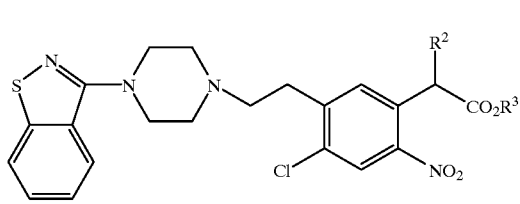

XI wherein $R^2$ is CN or $CO_3R^3$ and $R^3$ is $(C_1-C_6)$alkyl.

The compound of formula XI can then be treated with an acid at an elevated temperature to form the compound of formula XI wherein $R^2$ and $R^3$ are both hydrogen.

The compound of formula XI can then be treated with a $(C_1-C_6)$alkanol in the presence of an acidic esterification catalyst to form the compound of formula XI wherein $R^2$ is hydrogen and $R^3$ is $(C_1-C_6)$alkyl.

The compound of the formula XI, wherein $R^2$ is hydrogen, CN or $CO_2R^3$ and $R^3$ is hydrogen or $(C_1-C_6)$ alkyl, can then be treated with a reducing agent with the proviso that when $R^2$ is CN or $CO_2R^3$ and $R^3$ is $(C_1-C_6)$ alkyl the product of the reduction is heated with an acid to form ziprasidone.

Specific details of the reaction steps of converting compounds of the formula I into ziprasidone can be found in U.S. Pat. No. 5,359,068, issued Oct. 25, 1994.

Ziprasidone (hemihydrate or monohydrate) may be administered as a neuroleptic agent as described in above-mentioned U.S. Pat. Nos. 4,831,031 and 5,312,925 (the hemihydrate and monohydrate respectively). Administration to a human subject may be alone or, preferably, in combination with pharmaceutically acceptable carriers or diluents in a pharmaceutical composition, in accordance with standard pharmaceutical practice. The ziprasidone (hemihydrate or monohydrate) may be administered orally or parenterally including intravenously or intramuscularly. Suitable pharmaceutical carriers include solid diluents or fillers, and sterile aqueous solutions and various organic solvents. The pharmaceutical compositions are then readily administered in a variety of dosage forms, such as tablets, powders, lozenges, syrups, and injectable solutions. These pharmaceutical compositions, if desired, may contain additional ingredients such as flavorings, binders and excipients. Thus, for purposes of oral administration, tablets containing various excipients such as sodium citrate, calcium carbonate and calcium phosphate may be employed along with various disintegrants such as starch, aiginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredients therein may be controlled with various sweetening or flavoring agents, coloring matter or dyes and, if desired, emulsifying or suspending agents, together with diluents such as water, ethanol, propylene glycol, glycerin and combinations thereof.

For parenteral administration, a solution or suspension of ziprasidone (hemihydrate or monohydrate) in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intrapertioneal administration. The sterile aqueous media employed are all readily available by standard techniques known to those skilled in the art.

The effective dosage for ziprasidone (hemihydrate or monohydrate) depends on the intended route of administration and other factors such as age and weight of the subject, as generally known.

The following Examples illustrate the preparation of the intermediates and processes of the present invention. Commercial reagents were utilized without further purification. Melting points are uncorrected. NMR data are reported in parts per million (δ) and are referenced to the deuterium lock signal from the sample solvent. Unless otherwise stated, all mass spectrum were performed using electron impact (El, 70 •V) conditions. Unless otherwise indicated, chromatography refers to column chromatography performed using 32–63 μm silica gel and executed under nitrogen pressure (flash chromatography) conditions. High Pressure Liquid Chromatography (HPLC) was performed on a LDC Analytical constaMetric® 3200 HPLC (Thermo Separation Products Co.). A Zorbax®C8, 60 Å, 3.9×150 mm column (Mac-Mod Analytical, Inc., Chadds Ford, Pa. 19317) was used for HPLC analysis (mobile phase: 40% acetonitrile, 45% 0.05M potassium phosphate, monobasic ($KH_2PO_4$) adjusted to pH=6.0 with potassium hydroxide (KOH), 15% methanol; Flow Rate of 1.0 ml/minute; Detector: UV 229 nm; injector: 10 ul; Samples are prepared in mobile phase (0.05 mg/ml)). Room temperature refers to 20–25° C.

EXAMPLE 1

3-(1-Piperazinyl)-1,2-benzisothiazone hydrochloride

Method A

Bis(2-cyanophenyl)disulfide (20.0 g, 74.5 mmol), anhydrous piperazine (64.2 g, 745 mmol), dimethyl sulfoxide (12.8 g, 164 mmol), and isopropanol (24 mL) were added to a 500 mL round bottom flask equipped with a mechanical stirrer, thermometer, condenser topped with a nitrogen inlet and a connector leading to a bleach scrubber. After the flask was purged with nitrogen, the reactants were melted (at approximately 80° C.) and then heated to reflux (110°–126° C.). After 24 hours at reflux, the reddish solution was sampled for thin-layer chromatography (elution with methylene chloride/isopropanol/triethylamine, 15:5:1) which showed that the reaction was complete. The solution was cooled to 85–90° C., at which point water (130 mL) was added. The resulting slurry was cooled to 30–35° C. The reaction mixture was then concentrated at reduced pressure (bp=50–80° C. at 110 mm) to remove approximately 30 mL of distillate. The distillate was treated with bleach to destroy the dimethyl sulfide (DMS). Drager tubes (Drägerwack Ag Lübeck, Germany), which are selective for detecting ppm levels of dimethyl sulfide, showed that the reaction's headspace vapors contained less than 1 ppm residual DMS. A sample of the crude reaction mixture was analyzed by HPLC. The crude reaction mixture contained 3-(1-piperazinyl)-1,2-benzisothiazole (80%), 3,3'-(1,4-piperazinyl)-bis-1,2-benzisothiazole (4.6%), and 2-(1-piperazinyl)pyrazine (4%). After isopropanol (28 mL) and water (71 mL) were added, the slurry was cooled to 30° C., granulated for 0.5 hour, and then filtered through diatomaceous earth, e.g., Celite®, to remove 3,3'-(1,4-piperazinyl)-bis-(1,2-benzisothiazole. The filter cake was washed with 56 mL of an isopropanol/water (1:1) solution. Toluene (170 mL) was added to the warm (32° C.) filtrate, and then the separated aqueous layer was washed with fresh toluene (100 mL). The combined toluene layers were washed with water (100 mL) and then treated with decolorizing carbon, e.g., DARKO KB-B®, (2 g). The Celite® cake was rinsed with toluene (60 mL), and the combined wash and filtrate were concentrated at reduced pressure to 90 mL isopropanol (220 mL) was added to the concentrate and the yellowish solution was cooled to 20° C. The pH of the solution was slowly adjusted to 3.5–4.0 with 9.8 mL of concentrated hydrochloric acid. The resulting slurry was cooled to 0–5° C., granulated for 1 hour, and then filtered. The product cake was washed with cold isopropanol (80 mL), and then dried in vacuo at 40° C. for 24 hours. The title compound (43.2 g) was isolated as a light yellow solid in 77.6% yield (98.5% hplc purity). The spectroscopic and physical properties of the solid were identical to an authentic sample (Caution: compound is a strong irritant). $^1$H NMR ($D_2O$): δ7.80 (m, 2H), 7.49 (m, 1H), 7.35 (m, 1H), 3.58 (m, 4H), and 3.42 (m, 4H).

$^{13}$C NMR (dimethyl sulfoxide): δ162.72, 152,10, 128,15, 127.09, 124.63, 124,12, 121.21, 48.48, and 42.49

EXAMPLE 2

3-(1-Piperazinyl)-1,2-benzisothiazole•hydrochloride

Bis(2-cyanophenyl)disulfide (5.00 g, 18.6 mmol), anhydrous piperazine (8.02 g, 93.2 mmol), and isopropanol (5 mL) were combined under nitrogen and heated to reflux (115° C.). The yellow solution was heated at reflux (110–115° C.) for 23 hours and then cooled to 95° C. Water (30 mL) was added and the resulting suspension was cooled to 25° C. and filtered. The filter cake was washed with 12 mL of water/isopropanol solution (2:1). Toluene (50 mL) was then added to the combined wash and filtrate. The toluene layer was separated and the aqueous layer extracted with additional toluene (25 mL). The combined toluene layers were washed with water (20 mL), treated with activated charcoal (DARCO KB-B®) (0.5 g). filtered, and then concentrated at reduced pressure (42° C. at 700 mm Hg) to 12 mL. Isopropanol (30 mL) was added to the concentrate and then the pH was adjusted to 4.4 with concentrated hydrochloric acid. The resulting slurry was cooled to 0–5° C., granulated for 1 hour, and then filtered. The product cake was washed with cold isopropanol (10 mL) and dried in vacuo at 42° C. to give 3.22 g (34% overall yield) of 3-(1-piperazinyl)-1,2-benzisothiazole. The product was a single spot by thin-layer chromatography.

The pH of the aqueous layer was adjusted to 4.0 with concentrated hydrochloric acid, and then extracted with methylene chloride (40 mL). The methylene chloride solution was concentrated at reduced pressure to an oil which was then dissolved in methanol (19 mL). The solution was cooled in an ice bath and 10% aqueous hydrogen peroxide solution (7 mL) was added with stirring. After stirring for 10 minutes, thin-layer chromatography showed that the reaction was complete. Water (12 mL) was added and the slurry was granulated for 1.5 hours. Product was filtered and dried in vacuo at 40° C. to recover 1.64 grams (33% recovery) of bis(2-cyanophenyl)disulfide for recycle.

EXAMPLE 3

3-(1-Piperazinyl)-1,2-benzisothiazole•hydrochloride

Anhydrous piperazine (49.4 g, 0.57 mol) and t-butanol (10 mL) were added to a dry, 300 mL round bottom flask equipped with a mechanical stirrer, thermometer, condenser topped with a nitrogen inlet, and pressure-equalizing dropping funnel. After the flask was purged with nitrogen, it was heated to 100° C. in an oil bath. A solution of 3-chloro-1, 2-benzisothiazole (19.45 g, 0.11 mol) in t-butanol (10 mL) was added to the addition, funnel, and then slowly added to the reaction flask over 20 minutes to moderate an exothermic reaction (112–118° C.). Once addition was complete the yellow solution was heated to reflux (121° C.) and then maintained at reflux for 24 hours. Thin-layer chromatography showed that the reaction was complete. The reaction mixture was cooled to 85° C. and 120 mL of water was added. The hazy solution was filtered and the filter cake rinsed with 60 mL of t-butanol/water (1:1) solution. The pH of the combined filtrate and wash was adjusted to 12.2 with 50% aqueous caustic. The aqueous solution was extracted with toluene (200 mL), the layers were separated, and the aqueous layer was extracted with fresh toluene (100 mL). The combined toluene layers were washed with water (75 mL), and then the toluene solution was concentrated in vacuo at 48° C. to 90 mL. Isopropanl (210 mL) was added to the concentrate and then the pH was slowly adjusted to 3.8 with 7.6 mL of concentrated hydrochloric acid. The resulting slurry was cooled to 0° C., granulated for 45 min, and then filtered. The filter cake was washed with cold isopropanol (50 mL) and then dried in vacuo at 40° C. to afford 23.59 g (80% yield) of 3-(1-piperazinyl)-1,2-benzisothiazole hydrochloride as an off white solid.

EXAMPLE 4

3-(1-Piperazinyl)-1,2-benzisothiazole 3-(2-Cyanophenylthio)-1,2-benzisothiazole (0.25 g, 0.93 mmol), anhydrous piperazine (0.80, 9.32 mmol), and isopropanol (0.25 mL) were added to a 6 mL round bottom flask equipped with a magnetic stirring bar, reflux condenser topped with a nitrogen inlet, and thermometer. The flask was purged with nitrogen and then immersed in a 120° C. oil bath to give a yellow refluxing solution. After heating at 116–120° C. for 25 hour, the reddish solution was cooled to 25° C. and 5 mL of methanol was added. Thin-layer chromatography (methylene chloride/isopropanol/triethylamine, 15:5:1) showed that the reaction was essentially complete. The crude reaction solution was analyzed by high-pressure liquid chromatography to show that 3-(1-piperazinyl)-1,2-benzisothiazole was formed in 70% yield.

EXAMPLE 5

3-(1-Piperazinyl)-1,2-benzisothiazole

Anhydrous piperazine (17.2 g, 0.20 mol) and isopropanol (3.0 mL) were charged to a round bottom flask equipped with a mechanical stirrer, thermometer, condenser topped with a nitrogen inlet, and an addition tunnel. Once the flask was purged and then maintained under nitrogen, the mixture was heated to 90° C. to afford a solution. A solution of 1-(2-cyanophenylthio)piperazine (4.38 g, 20.0 mmol) in isopropanol (2.0 mL) was slowly added to the warm piperazine solution over 1 hour. Once the addition was complete, the solution was heated to reflux (118° C.) for 24 hours. The reddish solution was cooled to room temperature and then analyzed by HPLC. 3-(1-Piperazinyl)-1,2-benzisothiazole was formed in 55% yield by HPLC assay.

EXAMPLE 6

3-(2-Cyanophenylthio)-1,2-benzisothiazole

Method A

Bis(2-cyanophenyl)disulfide (1.25 g, 4.66 mmol), anhydrous piperazine (4.01 g, 48.6 mmol), and dimethyl sulfoxide (0.80 g, 10.3 mmol) in 15 mL of tetrahydrofuran were added to a 50 mL round bottom flask equipped with a magnetic stirring bar, thermometer, and condenser topped with a nitrogen inlet. After the flask was purged with nitrogen, the mixture was heated at reflux (75° C.) for 25 hours. The reaction mixture was cooled to 25° C., and the tetrahydrofuran was removed at reduced pressure. The resulting solid was dissolved in a 40 mL of a methylene chloride/water (1:1) mixture, the layers were separated, and the organic layer washed with water (20 mL). The methylene chloride solution was evaporated to afford a crude solid (0.85 g) which was crystallized from isopropanol (17 mL) to give light yellow crystals. After filtration, the product was dried in vacuo at 40° C. to give 0.39 g (31% yield) of 3-(2-cyanophenylthio)-1,2-benzisothiazole. Melting point 115.5–117° C. $^1$H NMR (CDCl$_3$): δ8.03 (m, 1H), 7.92 (m, 1H), 7.77 (m, 1H), 7.70 (m, 1H), 7.57 (m, 2H), and 7.48 (m, 2H), $^{13}$C NMR (CDCl$_3$): δ154.99, 152.30, 134,83, 134.56, 134.06, 133.24, 129.07, 128.51, 125.33, 123,29, 120.13, 117.13, and 116.95. Analytical calculated for $C_{14}H_8N_2S_2$ C, 62.66; H, 3.00; N, 10.44; S, 23.90. Found: C, 62.43; H, 3.01; N, 10.58; S, 24.05. A X-ray crystal structure was also obtained to confirm structure.

EXAMPLE 7

3-(2-cyanophenylthio)-1,2-benzisothiazole

Method B

Bis(2-cyanophenyl)disulfide (0.40 g, 1.48 mmol) and 2-mercaptobenzontrile (0.20 g, 1.48 mmol) were combined in 2 mL of isopropanol and were heated at reflux (90° C.) for 25 hours under a nitrogen (N$_2$) atmosphere. 3-(2-Cyanophenylthio)-1,2-benzisothiazole was formed in 69% yield by HPLC assay.

EXAMPLE 8

1-2-Cyanophenylthio)piperazine

Anhydrous piperazine (22.5 g, 261 mmol) and tetrahydrofuran (100 mL) were combined under a nitrogen atmosphere and then heated to 60–65° C. 3-Chloro-1,2-benzisothiazole (10.0 g, 59.0 mmol) was slowly added over one hour to the warm piperazine solution and then the resulting reddish solution was heated at 65° C. for 17 hours. Thin-layer chromatography (ethyl acetate/hexanes/triethylamine, 10:10:1) showed that the reaction was complete. The mixture was cooled to room temperature and then filtered. After toluene (100 mL) was added, the solution was concentrated at reduced pressure (40° C.) to one-half volume. The toluene solution was washed with water (100 mL), and the aqueous layer was extracted with fresh toluene (25 mL). The combined toluene layers were concentrated at reduced pressure to about 30 mL. After cooling the solution to 0–5° C. hexanes (50 mL) was slowly added. The resulting crystals were granulated for 1 hour at 0 to 5° C. filtered, and the cake was washed with fresh hexane (15 mL). After drying the solids for 18 hours at 23° C., 11.51 grams (89% yield) of a yellow crystalline solid (m.p.=67–71° C.) was isolated. The crude sulfenamide contained approximately 5% of 1,4-bis(2-cyanophenylthio)piperazine by NMR analysis. Title sulfenamide was stored at 0 to −10° C. to prevent slow conversion to 1,4-bis(2-cyanophenylthio) piperazine with heating or storage at room temperature. $^1$H NMR (CDCl$_3$): δ7.63 (m, 1H), 7.56 (m, 3H), 7.21 (m, 1H), 2.96 (m, 4H), and 2.87 (m, 4H). $^{13}$C NMR (CDCl$_3$): δ142.69, 133.55, 132.67, 128.14, 126.69, 116.80, 110.24, 57.34, and 47.06. HRMS Found: 220.0878; $C_{11}H_{13}N_3S$ Requires (FAB P+1): 220.0908.

What is claimed is:

1. A compound of the formula

IIa

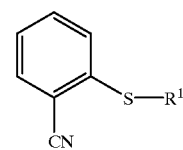

wherein R[1] is

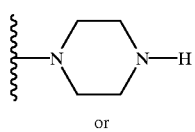
or

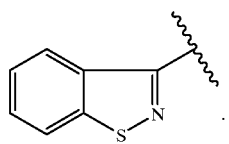

2. A process for preparing a compound of the formula

I

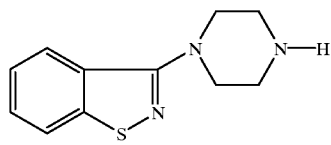

comprising reacting a compound of the formula

II

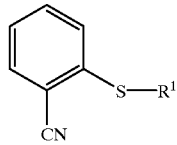

wherein R[1] is a

b
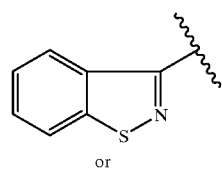
or c
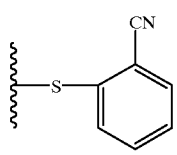

with piperazine at a temperature from about 80° C. to about 170° C.

3. A process according to claim 2, wherein R[1] is c
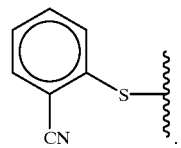

4. A process according to claim 3, wherein said piperazine is present in about 2 mole equivalents to about 15 mole equivalents relative to the amount of a compound of formula II.

5. A process according to claim 4, wherein said piperazine is present in about 10 mole equivalents relative to the amount of a compound of formula II.

6. A process according to claim 5, wherein the reaction of the compound of formula II with piperazine is performed in the presence of a piperazine clearing agent.

7. A process according to claim 6, wherein said piperazine clearing agent is isopropanol, pyridine or t-butanol.

8. A process according to claim 7, wherein said piperazine clearing agent is isopropanol.

9. A process according to claim 8, wherein the amount of said piperazine clearing agent, isopropanol, comprises 1.2 volumes relative to the weight of the compound of formula II.

10. A process according to claim 2, wherein the reaction of the compound of the formula II wherein R[1] is b
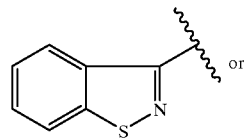
or c
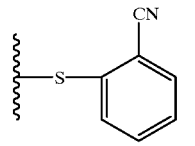

with piperazine is performed in the presence of a thiol oxidizing agent.

11. A process according to claim 10, wherein the reaction of said compound of formula II with piperazine and a thiol oxidizing agent is performed in the presence of a piperazine clearing agent.

12. A process according to claim 11, wherein R[1] is c
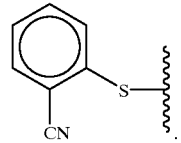

13. A process according to claim 12, wherein said thiol oxidizing agent is dimethyl sulfoxide, air, copper(II)salts, bisulfite, metabisulfite or hydrogen peroxide.

14. A process according to claim 13, wherein said piperazine clearing agent is isopropanol, pyridine or t-butanol.

15. A process according to claim 14, wherein said piperazine clearing agent is isopropanol.

16. A process according to claim 15, wherein said thiol oxidizing agent is dimethyl sulfoxide.

17. A process according to claim 16, wherein the amount of said thiol oxidizing agent, dimethyl sulfoxide, comprises 2–4 mole equivalents relative to the compound of formula II.

18. A process according to claim 17, wherein the amount of said piperazine clearing agent, isopropanol, comprises 1.2 volumes relative to the weight of the compound of formula II.

* * * * *